United States Patent [19]

Ingenito et al.

[11] 4,054,523

[45] Oct. 18, 1977

[54] CARDIOTOMY RESERVOIR WITH INTEGRAL FILTER

[75] Inventors: Donald R. Ingenito, Scotia; Gunnar E. Walmet, Schenectady, both of N.Y.

[73] Assignee: General Electric Company, Milwaukee, Wis.

[21] Appl. No.: 377,923

[22] Filed: July 10, 1973

[51] Int. Cl.² .............................................. B01D 35/02
[52] U.S. Cl. ................................. 210/188; 210/314; 210/436; 210/DIG. 23
[58] Field of Search .............. 210/314, 451, 188, 436, 210/455; 23/258.5; 214/214 R, 214 C, DIG. 3

[56] References Cited

U.S. PATENT DOCUMENTS

| | | | |
|---|---|---|---|
| 2,833,279 | 5/1958 | Gollan | 23/258.5 |
| 3,175,555 | 3/1965 | Ling | 23/258.5 |
| 3,701,433 | 10/1972 | Krakauer et al. | 210/436 |
| 3,747,769 | 7/1973 | Brumfield | 23/258.5 X |
| 3,768,653 | 10/1973 | Brumfield | 23/258.5 X |
| 3,769,162 | 10/1973 | Brumfield | 23/258.5 X |
| 3,795,088 | 3/1974 | Esmond | 210/DIG. 23 |

*Primary Examiner*—Frank A. Spear, Jr.
*Attorney, Agent, or Firm*—Thomas J. Bird; Edward A. Hedman; Rocco S. Barrese

[57] ABSTRACT

A reservoir for holding and reprocessing foamy shed blood prior to reintroduction to a patient, the reservoir comprising a holding chamber divided by a filter into two sub-chambers, a foam killing chamber in open communication with one of the sub-chambers, and inlet and outlet ports for the blood. The apparatus removes cell debris and filterable products of hemolysis and avoids the need to return chemical foam killers and collapsed foam to the patient's body.

10 Claims, 2 Drawing Figures

CARDIOTOMY RESERVOIR WITH INTEGRAL FILTER

This invention relates to a cardiotomy reservoir. More particularly, there is provided a reservoir for holding and reprocessing foamy shed blood prior to reintroduction to a patient, the reservoir comprising a holding chamber including an integral filter and a separate foam killing chamber which can be either inside or outside of the filtering chamber.

BACKGROUND OF THE INVENTION

Storage reservoirs are used to pick up and reprocess blood shed in the operating field. The blood is processed by removing the foam, which is easily generated by sucking operations, and also by filtering the defoamed blood before re-introducing it into the circuit and ultimately into the patient.

The basic need for such reservoirs is to permit collection of shed blood and then to feed it back into the patient. In many cardiovascular operations, too much blood is shed to permit outright discard, as is done in most other surgical procedures. On the other hand, such shed blood is apt to contain cellular and other debris which would embolize if infused directly back into the patient. Moreover the process of sucking the blood up is hemolytic in itself -- to the point of causing more damage even than pumps or oxygenators. Much foam is ordinarily generated and the blood which is actually suspended in the foam has been subjected to high shear rates as the film bubbles are formed and also there is an undesirable contact with an air interface. These factors cause blood damage and, although foaming has in the past been controlled by adding silicone antifoam agents, there are some reports that silicone itself is responsible for blood damage, and it is undesirable to have such chemical antifoams enter the body in small amounts, particularly as droplets or micro emboli.

There is now provided a combination cardiotomy reservoir and blood filter. The device serves as a storage reservoir for blood picked up from the operating field and then processes the blood by separating the foam and removing cell debris by filtration before reintroducing the blood into the circuit. In this novel device the reservoir and filter are combined into an integral unit; and the foam is killed and collected externally, then discarded.

Thus, the present invention provides a device which allows storage and return of blood to the patient with as little additional damage as possible. In contrast to separate filters requiring several hundred milliliters of blood for priming, the new device requires no additional priming volume because the filter is in the body of the reservoir. Other advantages in the new device are in greater ease of usage, improved ease of maintaining sterility, and ready adaptability to circuits which contain membrane oxygenators, where a filter in the primary circuit is of doubtful value. In addition, since defoaming is not needed in the main flow circuit, as in the case of bubble oxygenators, the introduction of chemical foam killers into the patient can be avoided entirely.

DESCRIPTION OF THE INVENTION

Figures 1, 2:
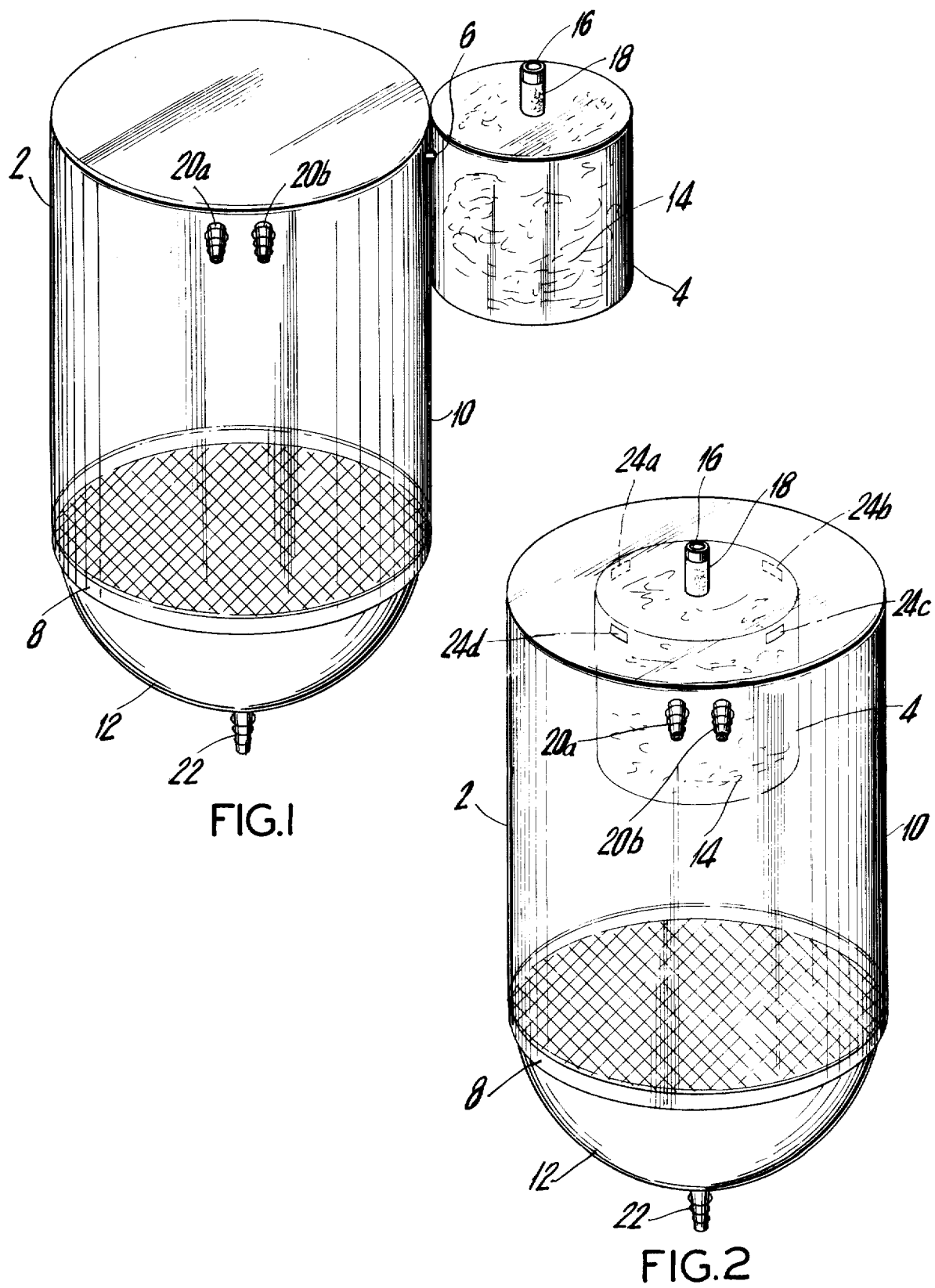
FIG. 1 is a perspective view of a reservoir with integral filter according to this invention, in which the foam killing chamber is located externally to the reservoir chamber.
FIG. 2 is a perspective view of another embodiment according to this invention, in which the foam killing chamber is located internally within one sub-chamber of the reservoir.

According to this invention, there are provided reservoirs for holding and reprocessing foamy shed blood prior to reintroduction to a patient, said reservoirs comprising a. a hollow holding and filtering chamber;

b. an integral filter dividing said chamber into first and second sub-chambers;

c. at least one blood inlet port in said first sub-chamber;

d. a foam killing hollow chamber for collecting and collapsing blood foam in open communication with said first sub-chamber, said foam killing chamber including an air vent port; and e. at least one blood outlet port in said second sub-chamber.

In preferred features of the invention, the first sub-chamber will be relatively larger in volume than the second sub-chamber. For example, the first sub-chamber will most preferably be from 5 to 20 times the volume of the second sub-chamber. It is also a preferred feature to provide that the foam killing chamber is relatively smaller in volume than the first sub-chamber; most preferably, the first sub-chamber will have from 2 to 8 times the volume of the foam killing chamber. In other preferred features, the foam killing chamber will be located either outside of the reservoir chamber, or else entirely within the first sub-chamber. Preferred results are obtained if the filter element includes openings in the range of 25 to 40 microns: and if the foam killing chamber includes a low density porous packing. A useful embodiment is one in which the holding and filtering chamber is distensible.

DESCRIPTION OF THE PREFERRED EMBODIMENTS

Referring to FIG. 1, there is illustrated a cardiotomy reservoir-filter having main collecting chamber 2 and foam killing chamber 4. Illustratively, chamber 2 will have a volume of about 1 liter and chamber 4 a volume of about 250 ml. Chambers 2 and 4 are connected through open conduit 6 near the top of each. Filter 8 is fixed in collecting chamber 2 dividing it into an upper first sub-chamber 10 and a lower second sub-chamber 12. The floor of sub-chamber 12 has a sloped bottom which facilitates complete drainage. Foam killing chamber 4 is filled with low density porous packing 14, which may be, for example, gauze, plastic scrim, loose screen, coarse, open celled plastic foam, and the like, which preferably, is coated with a material to aid in killing foam, such as a poly(dimethylsiloxane) fluid. As a coating material, an aqueous emulsion such as General Electric Silicone Fluid AF 72 is especially efficacious. Air vent tube 16, plugged with a small amount of porous material 18 coated with foam killing material is fitted to the top of foam killing chamber 4. This keeps any foam from overflowing from chamber 4. First sub-chamber 10 is provided with one or more blood inlet ports 20a, 20b, and sub-chamber 12 is fitted with one or more blood outlet ports 22.

Referring to FIG. 2, there is shown a reservoir-filter which differs from that of FIG. 1 only in having foam killing chamber 4 located within upper sub-chamber 10.

In this case, one or more connecting passageways 24 a, b, c and d are provided for the transfer of blood foam into foam killing chamber 4.

Referring to FIG. 1, in operation, blood mixed with air will enter main collecting reservoir 2 through ports 20a and 20b and will drain by gravity through filter 8 into second sub-chamber 12. Any entrained smaller bubbles will rise to the surface of the blood in first subchamber 10. Meanwhile, all of the free space in subchamber 10 above the liquid level will fill with the rather stable foam which is characteristic of blood. This foam contains only about 1–3% liquid by volume and is forced to expand through conduit 6 into foam killing chamber 4. On contact with porous packing 14, especially if the packing is pretreated with a chemical antifoam, e.g., a silicone fluid, the foam is almost instantaneously destabilized -- and collapses. Thus, that small amount of blood, which is carried in as foam, is collected in chamber 4. After sufficient blood is collected in main reservoir chamber 2, some of it can be drained off through outlet port 22 back to the patient circuit, in a conventional manner. And this can be done intermittently or continuously.

The device shown in FIG. 2 is operated in an entirely analogous fashion; in this case, however, the foam passes into chamber 4 through ports 24a–d.

For use with a membrane lung oxygenator (see the copending application of Gary W. Hammond, Donald R. Ingenito and Gunnar E. Walmet, Ser. No. 348,711, filed Apr. 6, 1973, now U.S. Pat. No. 3,907,504, the disclosure of which is incorporated herein by reference) outlet port 22 can remain open throughout the operation with a low blood level being continuously maintained by proper adjustment of flows between the cardiotomy reservoir and the compliant reservoir with which it is used.

For use with a conventional bubble oxygenator, on the other hand, the cardiotomy reservoir of this invention can also be arranged to drain through port 22 continuously into the oxygenator.

In any event, at the end of the surgical procedure, main collecting chamber 2 can be almost completely drained and the whole assembly discarded along with the damaged blood collected in foam killing chamber 4. Because only about 1–3% of the blood is lost to foam killing chamber 4, about 8 to 25 liters of blood can easily be processed in a 1 liter reservoir with a 250 ml. foam killing chamber, and this is abundant capacity for most procedures. If necessary, of course, increased capacity can be obtained either with a larger unit, or by using two units of the size described.

Filter 8 can vary widely in construction. It is convenient simply to provide a piece of fine weave polyester or polyolefin cloth held on a support frame. Alternately, filter 8 can be made with polyester or polyolefin fibers and it can simply be packed into second subchamber 12.

The reservoirs of FIGS. 1 and 2 are shown with rigid walls, and they can be constructed of any conventional material, e.g., metal, plastic, glass, and the like. It is obvious that the devices can be constructed as well from thick flexible plastic sheets, using only a rigid bottom to hold the filter and the exit port. Moreover, the porous packing in the foam killing chamber can help define that chamber's shape, while the main chamber can be distensible. The design of the entire unit is adaptable to easily interface with a suction pump on one end and a compliant venous reservoir on the other end and the entire circuit can be provided as one integral product. To save unnecessarily detailed explanation, the description of Ser. No. 348,711 relating to blood circuits — in which cardiotomy reservoirs, foam traps and filters are shown as components — is hereby incorporated by reference.

The above description demonstrates that the present invention provides a cardiotomy reservoir with integral filter and a foam killing chamber which avoids the need to return chemical antifoam and collapsed foam to the patient. In addition, the blood returned is clear of filterable debris. Moreover, only a small amount of blood is lost in the external foam killing process.

Many variations of the present invention are possible without departing from the spirit of scope of the appended claims.

We claim:

1. A reservoir for holding and reprocessing foamy shed blood prior to reintroduction to a patient, said reservoir comprising:
   a. a hollow holding and filtering chamber;
   b. an integral filter dividing said chamber into first and second sub-chambers;
   c. at least one blood inlet port in said first sub-chamber;
   d. a hollow foam killing chamber for collecting and collapsing blood foam in open communication with said first subchamber and removed from said integral filter, and positioned to permit the entrance of blood foam from said first sub-chamber and prevent the re-entrance or the entrance of the resultant collapsed blood into said first or second sub-chamber, said foam killing chamber including an air vent port; and
   e. at least one blood outlet port in said record sub-chamber.

2. A reservoir as defined in claim 1 wherein said first sub-chamber is relatively larger in volume than said second sub-chamber.

3. A reservoir as defined in claim 2 wherein the volume of said first sub-chamber is from 5 to 20 times the volume of said second sub-chamber.

4. A reservoir as defined in claim 2 wherein said foam killing chamber is disposed within said first sub-chamber.

5. A reservoir as defined in claim 1 wherein said foam killing chamber is relatively smaller in volume than the volume of said first sub-chamber.

6. A reservoir as defined in claim 5 wherein the volume of said first sub-chamber is from about 2 to about 8 times the volume of said foam killing chamber.

7. A reservoir as defined in claim 1 wherein said foam killing chamber is disposed externally of said holding and filtering chamber.

8. A reservoir as defined in claim 1 wherein the filter element has openings in the range of 25 to 40 microns.

9. A reservoir as defined in claim 1 wherein said foam killing chamber includes a low density porous packing.

10. A reservoir as defined in claim 1 wherein said holding and filtering chamber is distensible.

11. A reservoir for holding and reprocessing foamy shed blood prior to reintroduction to a patient, said reservoir comprising:
   a. a hollow holding and filtering chamber;
   b. an integral filter dividing said chamber into first and second sub-chambers, said filter having openings in the range of 25 to 40 microns;

c. at least one blood inlet port in said first sub-chamber;
d. a hollow foam killing chamber for collecting and collapsing blood foam in open communication with said first sub-chamber and removed from said integral filter, and positioned to permit the entrance of blood foam from said first sub-chamber and prevent the re-entrance or the entrance of the resultant collapsed blood into said first or second sub-chamber; said foam killing chamber including an air vent port; and
e. at least one blood outlet port in said second sub-chamber.

* * * * *